(12) United States Patent
Parker et al.

(10) Patent No.: US 7,470,370 B2
(45) Date of Patent: *Dec. 30, 2008

(54) PROCESS FOR REMOVAL OF IMPURITIES FROM MOTHER LIQUOR IN THE SYNTHESIS OF CARBOXYLIC ACID USING PRESSURE FILTRATION

(75) Inventors: Kenny Randolph Parker, Afton, TN (US); Robert Lin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/842,469

(22) Filed: Aug. 21, 2007

(65) Prior Publication Data

US 2007/0284317 A1 Dec. 13, 2007

Related U.S. Application Data

(60) Division of application No. 10/874,419, filed on Jun. 23, 2004, now Pat. No. 7,282,151, which is a continuation-in-part of application No. 10/455,016, filed on Jun. 5, 2003, now Pat. No. 7,410,632.

(51) Int. Cl.
*B01D 33/06* (2006.01)
*B01D 33/60* (2006.01)

(52) U.S. Cl. .............. 210/772; 210/774; 210/784; 210/806; 502/33; 562/414; 562/485; 562/494; 562/593

(58) Field of Classification Search ............... 210/772
See application file for complete search history.

(56) References Cited

U.S. PATENT DOCUMENTS 2,964,559 A 12/1960 Burney et al.
3,840,641 A 10/1974 Wampfler et al.
3,873,468 A 3/1975 Kobinata et al.
3,950,409 A 4/1976 Yokota et al.

(Continued)

FOREIGN PATENT DOCUMENTS

DE 2131470 A 6/1970

(Continued)

OTHER PUBLICATIONS

USPTO Office Action dated Sep. 25, 2007 for copending U.S. Appl. No. 11/655,396.

(Continued)

*Primary Examiner*—Peter A. Hruskoci
(74) *Attorney, Agent, or Firm*—Steven A. Owen; Bernard J. Graves, Jr.

(57) ABSTRACT

A process is disclosed that relates to the recovery of a metal catalyst from an oxidizer purge stream produced in the synthesis of carboxylic acid, typically terephthalic. More particularly, the process involves recovery of a metal catalyst from an oxidizer purge stream through the use of a pressure filter, the combining of water with a mother liquor to recover the metal catalyst and then subjecting an aqueous mixture so formed to a single stage extraction with an extraction solvent to produce an extract stream comprising organic impurities and a raffinate stream comprising the metal catalyst.

11 Claims, 3 Drawing Sheets

U.S. PATENT DOCUMENTS

| | | | |
|---|---|---|---|
| 3,996,271 | A | 12/1976 | Yokota et al. |
| 4,081,464 | A | 3/1978 | Marsh et al. |
| 4,158,738 | A | 6/1979 | Scott et al. |
| 4,185,073 | A | 1/1980 | Marsh et al. |
| 4,219,669 | A | 8/1980 | Tsuchiya et al. |
| 4,298,580 | A | 11/1981 | Harper et al. |
| 4,330,676 | A | 5/1982 | Moxham |
| 4,356,319 | A | 10/1982 | Roffia et al. |
| 4,769,489 | A | 9/1988 | Abrams et al. |
| 4,892,972 | A | 1/1990 | Schroeder et al. |
| 4,914,230 | A | 4/1990 | Abrams et al. |
| 4,939,297 | A | 7/1990 | Browder et al. |
| 5,200,557 | A | 4/1993 | Gee et al. |
| 5,643,468 | A | 7/1997 | Ure |
| 5,676,847 | A | 10/1997 | Yamamoto et al. |
| 5,705,682 | A | 1/1998 | Ohkashi et al. |
| 5,770,765 | A | 6/1998 | Ohkashi |
| 5,840,965 | A | 11/1998 | Turner et al. |
| 5,916,422 | A | 6/1999 | Kimura et al. |
| 5,955,394 | A | 9/1999 | Kelly |
| 6,054,610 | A | 4/2000 | Lee et al. |
| 6,133,476 | A | 10/2000 | Lin |
| 6,153,790 | A | 11/2000 | June et al. |
| 6,562,997 | B2 | 5/2003 | Sikkenga et al. |
| 7,074,954 | B2 | 7/2006 | Sheppard et al. |
| 7,132,566 | B2 | 11/2006 | Sumner et al. |
| 7,273,559 | B2 * | 9/2007 | Gibson et al. ............... 210/712 |
| 7,282,151 | B2 * | 10/2007 | Parker et al. ............... 210/634 |
| 7,291,270 | B2 * | 11/2007 | Gibson et al. ............... 210/650 |
| 2001/0041811 | A1 | 11/2001 | Sikkenga et al. |
| 2002/0016500 | A1 | 2/2002 | Matsumoto et al. |
| 2002/0193630 | A1 | 12/2002 | Lin et al. |
| 2004/0225148 | A1 | 11/2004 | Isogai et al. |
| 2004/0244536 | A1 | 12/2004 | Lin |
| 2004/0245176 | A1 | 12/2004 | Parker et al. |
| 2004/0249207 | A1 | 12/2004 | Lin et al. |
| 2004/0249208 | A1 | 12/2004 | Lin et al. |
| 2007/0205153 | A1 | 9/2007 | Parker et al. |
| 2007/0208195 | A1 | 9/2007 | Gibson et al. |
| 2007/0208196 | A1 | 9/2007 | Parker et al. |
| 2007/0208197 | A1 | 9/2007 | Gibson et al. |
| 2007/0208198 | A1 | 9/2007 | Parker et al. |
| 2007/0208199 | A1 | 9/2007 | Parker et al. |
| 2007/0213557 | A1 | 9/2007 | Seiki et al. |

FOREIGN PATENT DOCUMENTS

| | | |
|---|---|---|
| EP | 0 181 127 A2 | 5/1986 |
| EP | 0 764 627 A1 | 3/1997 |
| EP | 0 579 715 B1 | 8/1997 |
| EP | 1 484 305 A1 | 8/2004 |
| EP | 1 484 306 A1 | 8/2004 |
| GB | 892766 A | 3/1962 |
| GB | 1407705 | 9/1975 |
| GB | 2067563 A | 7/1981 |
| JP | 46-14339 B | 11/1974 |
| JP | 51-145488 A | 12/1976 |
| JP | 49-123191 A | 2/1979 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | 92/18453 | 10/1992 |
| WO | 92/18454 A1 | 10/1992 |
| WO | 93/24441 A | 12/1993 |
| WO | 97/27168 A1 | 7/1997 |
| WO | 97/30963 A | 8/1997 |
| WO | 00/31014 A1 | 6/2000 |
| WO | 01/55075 A2 | 8/2001 |

OTHER PUBLICATIONS

USPTO Office Action dated Sep. 25, 2007 for copending U.S. Appl. No. 11/655,395.

USPTO Notice of Allowance dated Dec. 3, 2007 for copending U.S. Appl. No. 10/455,017.

USPTO Notice of Allowance dated Jan. 15, 2008 for copending U.S. Appl. No. 10/455,016.

BHS—Werk Sonthofen, *BHS-FEST Pressure Filter,* 1990, pamphlet, Santhofen, West Germany.

USPTO Office Action dated Oct. 20, 2004 for U.S. Appl. No. 10/455,017.

USPTO Office Action dated Jun. 6, 2005 for U.S. Appl. No. 10/455,017.

USPTO Office Action dated Nov. 10, 2005 for U.S. Appl. No. 10/455,017.

USPTO office action dated Jul. 19, 2006 for copending U.S. Appl. No. 10/455,017.

USPTO office action dated Jul. 19, 2006 for copending U.S. Appl. No.10/455,018.

USPTO office action dated Dec. 27, 2006 for copending U.S. Appl. No. 10/455,018.

USPTO office action dated Jul. 19, 2006 for copending U.S. Appl. No. 10/455, 016.

USPTO office action dated Jan. 18, 2007 for copending U.S. Appl. No. 10/455,017.

USPTO office action dated Nov. 30, 2006 for copending U.S. Appl. No. 10/975,256.

USPTO office action dated Nov. 30, 2006 for copending U.S. Appl. No. 10/975,252.

USPTO office action dated May 11, 2007 for copending U.S. Appl. No. 10/455,017.

USPTO office action dated May 14, 2007 for copending U.S. Appl. No. 10/455,018.

USPTO Office Action dated May 17, 2007 for copending U.S. Appl. No. 11/201,512.

USPTO Office Action dated Jul. 6, 2007 for copending U.S. Appl. No.11/455,016.

Treybal, Robert E., "Stagewise Contact, Single-Stage Extraction," Mass-Transfer Operations, Third Edition, 1980, pp. 490-555, McGraw-Hill Book Company.

Copending U.S. Appl. No. 10/455,016 filed Jun. 5, 2003, Robert Lin.

Copending U.S. Appl. No. 10/455,017 filed Jun. 5, 2003, Robert Lin et al.

Copending U.S. Appl. No. 10/455,018 filed Jun. 5, 2003, Robert Lin et al.

Copending U.S. Appl. No. 10/874,419 filed Jun. 23, 2004, Kenny Randolph Parker et al.

Copending U.S. Appl. No. 10/948,591 filed Sep. 24, 2004, Robert Lin et al.

Copending U.S. Appl. No. 10/948,678 filed Sep. 24, 2004, Robert Lin et al.

Copending U.S. Appl. No. 10/975,256 filed Oct. 28, 2004, Philip Edward Gibson et al.

Copending U.S. Appl. No. 10/975,252 filed Oct. 28, 2004, Philip Edward Gibson et al.

Copending U.S. Appl. No. 11/181,214 filed Jul. 14, 2005, Robert Lin et al.

Copending U.S. Appl. No. 11/181,449 filed Jul. 14, 2005, Robert Lin et al.

Copending U.S. Appl. No. 11/201,512 filed Aug. 11, 2005, Robert Lin et al.

Copending U.S. Appl. No. 11/201,799 filed Aug. 11, 2005, Robert Lin et al.

Copending U.S. Appl. No. 11/655,395 filed Jan. 19, 2007, Philip E. Gibson et al.

Copending U.S. Appl. No. 11/839,575 filed Aug. 16, 2007, Philip E. Gibson et al.

Copending U.S. Appl. No. 11/655,317 filed Jan. 19, 2007, Philip E. Gibson et al.
Copending U.S. Appl. No. 11/839,578 filed Aug. 16, 2007, Philip E. Gibson et al.
Copending U.S. Appl. No. 11/839,582 filed Aug. 16, 2007, Philip E. Gibson et al.
Copending U.S. Appl. No. 11/655,396 filed Jan. 19, 2007, Kenny R. Parker et al.
Copending U.S. Appl. No. 11/839,573 filed Aug. 16, 2007, Kenny R. Parker et al.
Notice of Allowance dated Jul. 18, 2007 for copending U.S. Appl. No. 10/975,256.
Notice of Allowance dated Aug. 1, 2007 for copending U.S. Appl. No. 10/975,252.
USPTO Office Action dated Oct. 16, 2007 for copending U.S. Appl. No. 11/655,317.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
USPTO Office Action dated Mar. 4, 2008 for copending U.S. Appl. No. 11/839,575.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO Office Action dated Mar. 5, 2008 for copending U.S. Appl. No. 11/655,396.
USPTO Office Action dated Mar. 7, 2008 for copending U.S. Appl. No. 10/948,591.
USPTO Office Action dated Mar. 14, 2008 for copending U.S. Appl. No. 19/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,251 filed Mar. 18, 2008, Robert Lin et al.
Copending U.S. Appl. No. 12/050,253 filed Mar. 18, 2008, Robert Lin et al.
Copending U.S. Appl. No. 12/050,256 filed Mar. 18, 2008, Robert Lin et al.
Copending U.S. Appl. No. 12/050,258 filed Mar. 18, 2008, Robert Lin et al.
USPTO Office Action dated Apr. 4, 2008 for copending U.S. Appl. No. 11/181,449.
USPTO Office Action dated Apr. 25, 2008 for copending U.S. Appl. No. 11/181,214.
USPTO Notice of Allowance dated Oct. 1, 2008 for copending application 10/948,591.

* cited by examiner

PROCESS FOR REMOVAL OF IMPURITIES FROM MOTHER LIQUOR IN THE SYNTHESIS OF CARBOXYLIC ACID USING PRESSURE FILTRATION

CROSS REFERENCE TO RELATED APPLICATION

This application is a divisional of application Ser. No. 10/874,419, entitled "Process for Removal of Impurities from Mother Liquor in the Synthesis of Carboxylic Acid using Pressure Filtration", filed Jun. 23, 2004 now U.S. Pat No. 7,282,151 which is a continuation-in-part of U.S. application Ser. No. 10/455,016, filed Jun. 5, 2003 now U.S. Pat No. 7,410,632. The foregoing applications are hereby incorporated by reference.

FIELD OF INVENTION

This invention relates to the recovery of a metal catalyst from an oxidizer purge stream produced in the synthesis of carboxylic acid, typically terephthalic acid, while utilizing pressure filtration. More particularly, the process involves the combining of water with a mother liquor to recover the metal catalyst and then subjecting an aqueous mixture so formed to a single stage extraction with an extraction solvent to remove organic impurities to produce an extract stream and a raffinate stream comprising the metal catalyst.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities formed as a result of the oxidation of paraxylene.

Terephthalic acid (TPA) is an intermediate in the production of polyesters for plastics and fiber applications. Commercial processes for the manufacture of TPA are often based on the heavy-metal catalyzed oxidation of p-xylene, generally with a bromide promoter in an acetic acid solvent. Due to the limited solubility of TPA in acetic acid under practical oxidation conditions, a slurry of TPA crystals is usually formed in the oxidation reactor. Typically, the TPA oxidizer slurry is withdrawn from the reactor and TPA solids are separated from the oxidizer mother liquor using conventional solid-liquid separation techniques. The oxidizer mother liquor, which contains most of the catalyst and promoter used in the process, is recycled to the oxidation reactor. Aside from the catalyst and promoter, the oxidizer mother liquor stream also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions formed as a result of the oxidation of p-xylene to terephthalic acid. Patents disclosing the production of terephthalic acid such as U.S Pat. Nos. 4,158,738 and 3,996,271 are hereby incorporated by reference in their entirety to the extent that they do not contradict statements herein.

The TPA solids undergo a solid-liquid separation wherein fresh solvent is utilitized to displace a major portion of the liquid component of the oxidizer mother liquor. After drying, the TPA solids are contaminated with impurities that were present in the oxidizer mother liquor since these impurities may be incorporated into the TPA solids. Impurities are also present due to occlusions in the TPA crystal structure and due to incomplete removal of the oxidizer mother liquor by the fresh solvent wash.

Many of the impurities in the oxidizer mother liquor stream that are recycled are relatively inert to further oxidation. Such impurities include, for example, isophthalic acid, phthalic acid and trimellitic acid. Impurities, which may undergo further oxidation are also present, such as, for example, 4-carboxybenzaldehyde, p-toluic acid and p-tolualdehyde. Oxidation inert impurities tend to accumulate in the oxidizer mother liquor upon recycle. The concentration of these inert impurities will increase in the oxidizer mother liquor until an equilibrium is reached whereby the rate of removal of each impurity via the TPA product balances with the rate of formation and the rate of addition to the oxidation process. The normal level of impurities in commercial crude TPA makes it unsuitable for direct use in most polymer applications.

Conventionally, crude TPA has been purified either by conversion a dimethyl ester or by dissolution in water with subsequent hydrogenation over standard hydrogenation catalysts. More recently, secondary oxidative treatments have been used to produce polymer-grade TPA. It is desirable to minimize the concentration of impurities in the mother liquor and thereby facilitate subsequent purification of TPA. In some cases, it is not possible to produce a purified, polymer-grade TPA unless some means for removing impurities from the oxidizer mother liquor stream is utilized.

One technique for impurity removal from a recycle stream commonly used in the chemical processing industry is to draw out or "purge" some portion of the recycle stream. Typically, the purge stream is simply disposed of or, if economically justified, subjected to various treatments to remove undesired impurities while recovering valuable components. One example is U.S. Pat. No. 4,939,297 herein incorporated by reference in their entirety to the extent that they do not contradict statements herein. The amount of purge required for control of impurities is process-dependent; however, a purge amount equal to 10-40% of the total oxidizer mother liquor stream is usually sufficient to produce TPA adequate as feedstock for commercial polymer manufacture. In the production of TPA, the percentage purge of the oxidizer mother liquor stream purge necessary to maintain acceptable impurity concentrations, coupled with the economic value of the metal catalyst and solvent components in the oxidizer purge stream, make simple disposal of the oxidizer purge stream economically unattractive. Thus, there is a need for a process that recovers essentially all of the valuable metal catalysts and acetic acid contained in the oxidizer purge stream while removing a major portion of the impurities present in the oxidizer purge stream. The metal catalyst can be recovered in an active form suitable for reuse by direct recycling to the p-xylene oxidation step.

This invention is a marked improvement over a typical purge process. Some of the advantages are:

1) enhanced operability and reliability due to reduction in plugging potential;
2) reduction in overall energy usage;
3) reduction in the amount of water to the solvent extraction step.

The invention enhances the impurity removal efficacy of the process, and the operability of the process compared to the existing processes. In addition it should be noted that this invention does not just apply to the crude TPA process but any process that produces an oxidizer purge stream where recovery of metal catalyst is needed.

SUMMARY OF THE INVENTION

This invention relates to removal of impurities and the recovery of a metal catalyst from an oxidizer purge stream produced in the synthesis of carboxylic acids, typically terephthalic acid. More particularly, the process involves the combining of water with a mother liquor to recover the metal catalyst and then subjecting an aqueous mixture so formed to a single stage extraction with an extraction solvent to produce an extract stream and a raffinate stream comprising a metal catalyst.

It is an object of this invention to provide a process to recover a metal catalyst stream from an oxidizer purge stream through the use of a pressure filter.

It is yet another object of this invention to provide a process for removal of impurities and the recovery of a metal catalyst stream from an oxidizer purge stream produced in the synthesis of carboxylic acid, incorporating the use of a pressure filter.

In a first embodiment of this invention, a process is provided. The process comprises:
- (a) filtering a super concentrated purge slurry in a solid-liquid separation zone to form a filter cake and a mother liquor;
- (b) washing said filter cake with a wash feed in said solid-liquid separation zone to form a washed cake and a wash filtrate; and optionally dewatering said wash filter cake in said solid-liquid separation zone to form a dewatered cake; wherein said solid-liquid separation zone comprises at least one pressure filtration device.

In another embodiment of the invention, a process is provided. The process comprises:
- (a) subjecting an oxidizer purge stream comprising a carboxylic acid, a metal catalyst, impurities, water and a solvent to evaporation in a first evaporator zone to produce a vapor stream and a concentrated purge slurry; and
- (b) subjecting said concentrated purge slurry to evaporation in a second evaporator zone to produce a solvent rich stream and a super concentrated purge slurry wherein said second evaporator zone comprises an evaporator zone operated at a temperature of about 20° C. to about 70° C.;
- (c) filtering said super concentrated purge slurry in a solid-liquid separation zone to form a filter cake and a mother liquor;
- (d) washing said filter cake with a wash feed in said solid-liquid separation zone to form a washed cake and a wash filtrate; and optionally dewatering said washed cake in said solid-liquid separation zone to form a dewatered cake; wherein said solid-liquid separation zone comprises at least one pressure filtration device.

In another embodiment of the invention, a process to recover a metal catalyst from an oxidizer purge stream is provided. The process comprises:
- (a) subjecting said oxidizer purge stream comprising a carboxylic acid, said metal catalyst, impurities, water and a solvent to evaporation in a first evaporator zone to produce a vapor stream and a concentrated purge slurry;
- (b) subjecting said concentrated purge slurry in a second evaporator zone to form a solvent rich stream and a super concentrated purge slurry;
- (c) filtering a super concentrated purge slurry in a solid-liquid separation zone to form a filter cake and a mother liquor;
- (d) washing said filter cake with a wash feed in said solid-liquid separation zone to form a washed cake and a wash filtrate; and optionally dewatering said washed cake in said solid-liquid separation zone to form a dewatered cake; wherein said solid-liquid separation zone comprises at least one pressure filtration device;
- (e) mixing in a mixing zone water and optionally an extraction solvent with said mother liquor and all or a portion of the said wash filtrate to form an aqueous mixture;
- (f) contacting an extraction solvent with said aqueous mixture in an extraction zone to form an extract stream and a raffinate stream; and
- (g) separating said extract stream in a separation zone to form a high boiling point organic impurities stream and a recovered extraction solvent stream.

These objects, and other objects, will become more apparent to others with ordinary skill in the art after reading this disclosure.

DESCRIPTION OF THE INVENTION

Figure 1:
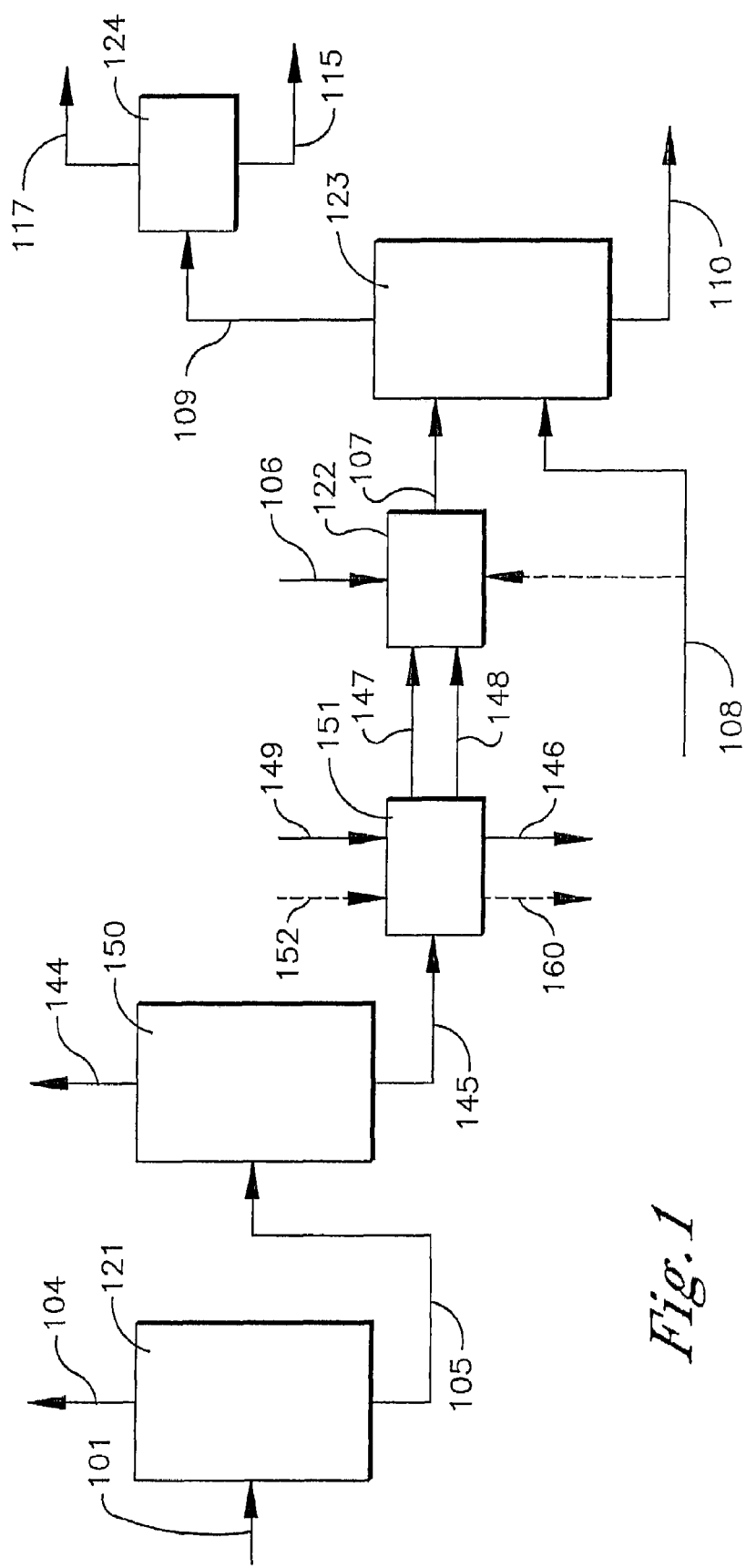
FIG. 1 illustrates different embodiments of the invention wherein a process to recover a metal catalyst from an oxidizer purge stream 101, and a process for separating organic impurities from a super concentrated purge slurry 145 is provided.
Figure 2:
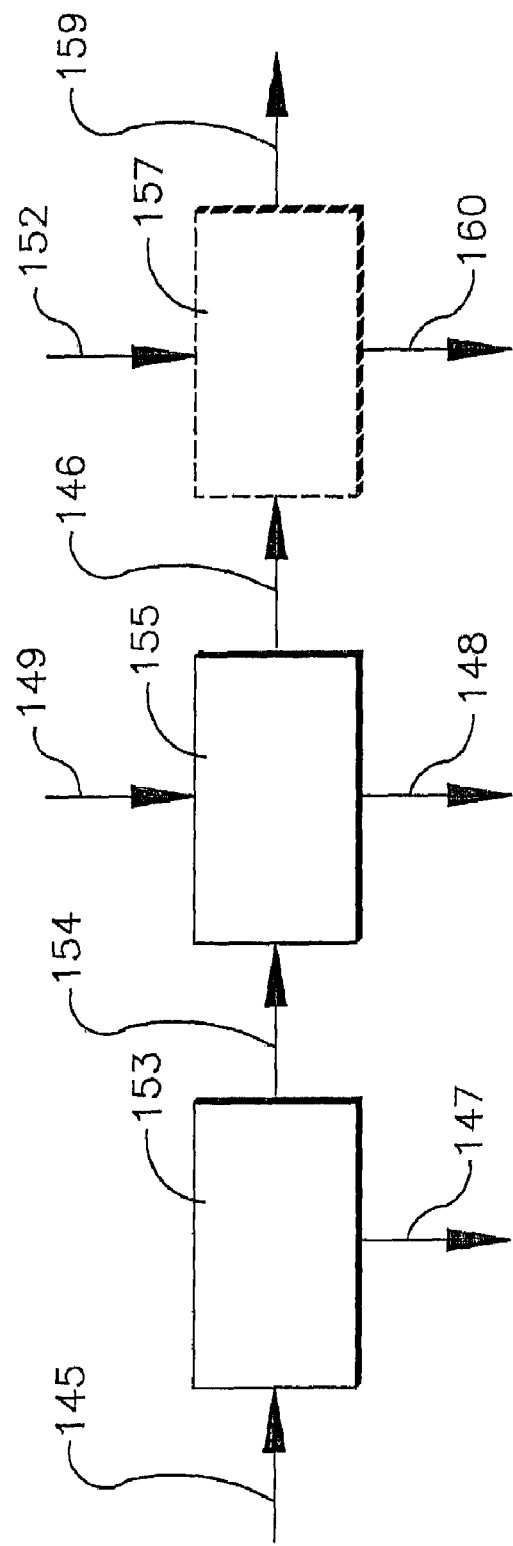
FIG. 2 illustrates an embodiment of the invention of the process occurring in the solid-liquid separation zone 151 which comprises a filtration zone 153, a washing zone 155, and optionally a dewatering zone 157.

In one embodiment of this invention, a process to recover a metal catalyst from an oxidizer purge stream 101 is provided as shown in FIG. 1 and FIG. 2. The process comprises the following steps.

Step (a) comprises subjecting an oxidizer purge stream 101 to evaporation in a first evaporator zone 121 to produce a vapor stream 104 and a concentrated purge slurry 105.

The oxidizer purge stream 101 is withdrawn from a carboxylic acid oxidative synthesis process. The oxidizer purge stream 101 serves as the feed stream to the present process. The oxidizer purge stream 101 comprises carboxylic acid, water, a solvent, the metal catalyst and impurities. The impurities comprise organic bromides, corrosion metals, p-xylene oxidation by-products, and impurities derived as a result of impurities in the p-xylene. The organic bromides may be used as promoters in the oxidation reaction. Examples of corrosion metals are iron and chromium compounds, which inhibit, reduce or entirely destroy the activity of the metal catalyst. Aside from the catalyst and promoter, the oxidizer mother liquor stream also contains by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid.

Carboxylic acids include aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic acid, isophthalic acid, trimellitic acid, naphthalene dicarboxylic acid, 2,5-diphenylterephthalic acid and mixtures thereof.

Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 8:1 and about 20:1. Throughout the specification, acetic acid will be referred to as the solvent. However, it should be appreciated that other suitable solvents, such as those disclosed previously, may also be utilized.

In the first step of the present process, the oxidizer purge stream 101 is concentrated by conventional means in a first evaporator zone 121 comprising an evaporator to produce a vapor stream 104 and a concentrated purge slurry 105. The evaporator is operated at atmospheric or slightly superatmospheric conditions, generally from about 1 atmosphere to about 10 atmospheres. The vapor stream 104 comprises a majority of the water and solvent, and the concentrated purge slurry 105 comprises the remainder of the water and solvent not removed from the oxidizer purge stream 101. The evaporation removes about 50 wt % to about 80 wt % of the solvent and water, typically acetic acid and water, which are present in the oxidizer purge stream 101.

Step (b) subjecting said concentrated purge slurry 105 to evaporation in a second evaporator zone 150 to produce a solvent rich stream 144 and said super concentrated purge slurry 145.

The second evaporator zone 150 comprises at least one evaporator operated at vacuum conditions. The evaporation can be conducted at a temperature from about 20° C. to about 70° C.; another range is from about 30° C. to about 50° C. The combination of evaporators 121 and 150 are operated so as to concentrate the oxidizer purge stream as represented by stream 101 to a condition wherein about 75 wt % to about 99 wt % of the solvent and water, typically acetic acid and water, is removed. Another range for operation of the combination of evaporators 121 and 150 to concentrate the oxidizer purge stream as represented by stream 101 to a condition wherein about 85 wt % to about 99 wt % of the solvent and water, typically acetic acid and water, is removed. Further, ranges stated in this disclosure and the claims that follow should be understood to disclose the entire range specifically and not just the end point(s). For example, disclosure of the range 0 to 10 should be taken to specifically disclose 2, 2.5, 3.17 and all other number subsumed and not just 0 and 10.

In an embodiment of the present invention, the condition of the super concentrated purge slurry 145 can be as a solid-liquid mixture with only enough solvent to provide pumpability.

Step (c) comprises filtering a super concentrated purge slurry 145 in a solid-liquid separation zone 151 to form a filter cake 154 and a mother liquor 147; and Step (d) washing said filter cake 154 with a wash feed 149 in said solid-liquid separation zone 151 to form a washed cake 146 and a wash filtrate 148; and optionally dewatering said washed cake 146 in said solid-liquid separation zone 151 to form a dewatered cake 159; wherein said solid-liquid separation zone 151 comprises at least one pressure filtration device;

The super concentrated purge slurry 145 is introduced in the solid-liquid separation zone 151 comprising a filtration zone 153 and a washing zone 155 and optionally a drying zone 157 as shown in FIG. 2. The filtration zone 153 comprises a filter cell, or a series of filter cells, physically situated to permit a filter cake 154 to develop a distribution across the area of the filter cell to hinder or prevent the channeling of wash feed 149 through the filter cake 154.

Suitably, a filter cake 154 of at least 0.25 inch in depth to about 8 inches in depth, preferably at least 0.5 inch in depth, preferably at least 1 inch in depth, and even more preferably about 2 to about 4 inches in depth is distributed over the area of the filter cell. The washed cake, 146, can be recovered or further treated, recycled and/or sent to waste treatment facilities.

Upon obtaining a suitable or preferred height of filter cake 154, about 0.5 inch to 4 inches, the filter cake 154 leaves the filtration zone 153 which comprises a filter or series of filters and enters a washing zone 155 where the filter cake 154 is contacted with a wash feed 149. There is sufficient pressure across the filter cake 154 to allow a reservoir or buildup of the wash feed 149 over the filter cake 154 to a suitable depth, preferably to a minimum depth of 0.25 inch. A pressure gradient of at least 0.5 psi, preferably from about 5 psi to about 65 psi, across the filter cake 154 and the reservoir of wash feed 149 can be applied to displace any solute in the filter cake 154 with wash feed 149.

A filter cake 154 depth of at least 0.5 inch is suitable to obtain a filter cake 154 of sufficient compactness to furnish a wash vehicle, i.e. the filter cake 154, from which a wash filtrate 148 containing a solute from the filter cake 154 can be removed efficiently by displacement washing. If the filter cake depth 154 is less than about 0.25 inch, channeling of wash feed 149 in the filter cake 154 can occur resulting in non-uniform washing of the filter cake 154.

Because of the loss of efficiency in displacement washing of the filter cake 154, a minimum filter cake 154 depth of at least 0.25 inch, of purified terephthalic acid is preferred.

A minimum liquid height above the filter cake 154 surface is required to ensure that displacement washing occurs. This height must be sufficient to ensure that the filter cake 154 surface is completely covered with wash feed 149. If the filter cake 154 surface is not covered with wash feed 149, bypassing of the wash feed 149 can occur without adequate displacement of the solute in the filter cake 154. Because of irregularities in the filter cake 154 surface, a minimum liquid height of about 0.25 inch is preferred above the filter cake 154 surface.

It has been found that displacement of the solute from the filter cake 154 using the wash feed 149 at high pressure permits an efficient separation of catalyst metals from the filter cake 154. Another benefit of high pressure is the reduction of wash feed 149 required to recover cobalt as shown in the examples.

Utilization of added stages in the solid-liquid separation zone 151 can decrease the amount of wash feed 149 required to reduce the total amount of metal catalyst retained in the filter cake 154. It is convenient therefore that a suitable number of stages of positive displacement washing be used to minimize total wash feed 149 used in displacement washing to reduce need for downstream waste treatment facilities.

It is understood that a multiple stages of the displacement washing procedure can replace a single stage displacement washing procedure wherein the quantity of wash feed 149 is sufficient to obtain at least 80% recovery of the metal catalyst from the super concentrated slurry 145 to the mother liquor 147 and the wash filtrate 148. Additionally, a procedure utilizing multiple stages of counter-current washing can be useful if reduction of the amount of wash feed 149 is determined to be advantageous.

In the process of the instant invention, a super concentrated purge slurry 145 is introduced into one or more of a series of filter cells physically situated to permit a filter cake 154 of requisite thickness to develop.

Upon obtaining a minimum height of filter cake 154, about 0.25 to about 4 inches, the filter cake 154 leaves the filter or series of filters and enters a washing zone 155 where the filter cake 154 is washed with a wash feed 149. Pressure can then be applied to the wash feed 149 to displace the solute (i.e. the liquid and any dissolved compounds such as metal catalyst in the filter cake) of the filter cake 154. Upon displacement of the solute with the wash feed, the filter cake 154 can be discharged from the filtration zone 155 by any suitable means and the cycle repeated. In an embodiment of the invention the ratio of wash feed 149 to filter cake 154 discharge is within the range of from about 1:20 to about 20:1 to reduce the level of metal catalyst in the filter cake by greater than 95%.

Equipment for performing the requisite washing cycle can comprise a series of filter cells maintained in a suitable position to permit a wash feed 149 flood to develop over the filter cells. In one embodiment of the invention, suitable equipment can comprise a rotary drum pressure filter with multiple filter cells, fitted with a means for discharging washed cake 146 from the filter cells. The filter cake 154 can be washed for as many times as required to develop a minimum concentration of metal catalyst in the washed cake 146 before discharging the washed cake 146 from the rotary drum filter.

A suitable pressure filter which can be adapted to the requirements of the instant invented process is a BHS-FEST™ rotary drum pressure filter, BHS-WERK, Sonthofen, D-8972, Sonthofen, West Germany, although other pressure filters which can accomplish the required operation can be used. Examples of other devices that can used in the solid-liquid separation zone include 151, but are not limited to; pressure belt filters, filter presses, centrifuges, pressure leaf filters, and cross-flow filters. The pressure filter can be operated at temperature and pressure sufficient to obtain at least 80% recovery of the metal catalyst from the solute of the mother liquor 147. Preferably the pressure filter can be operated at a temperature of about 25° C. to about 160° C., and a pressure of 1 atmospheres to 50 atmospheres.

In the operation of the BHS-FEST™ filter, a rotary drum contains a series of filter cells located on the periphery of the rotating drum. As the drum rotates, the filter cells receive a super concentrated purge slurry 145 and a filter cake 154 builds to a requisite depth. The mother liquor 147 is produced by filtration of the super concentrated purge slurry 145. Upon rotation of the drum, the filter cake 154 enters a washing zone 155 where reservoir of wash feed 149 is built up over the filter cake 154 to a required depth. The applied pressure to the wash feed reservoir forces the water through the filter cake 154 to displace the solute (with dissolved metal catalyst) retained in the super concentrated purge slurry 145 to produce a washed cake 146. Upon further rotation of the drum, the wash cycle can be repeated at least three more times if necessary in a counter current fashion, after which the system pressure is released with attendant temperature decrease to an ambient conditions. Optionally, the washed cake 146 can be dewatered in a dewatering zone 157 with a vapor via conduit 152 to produce a dewatered cake 159 and a humid vapor 160. The resultant dewatered cake 159 can then be discharged from the drum by any conventional means.

Figure 3:
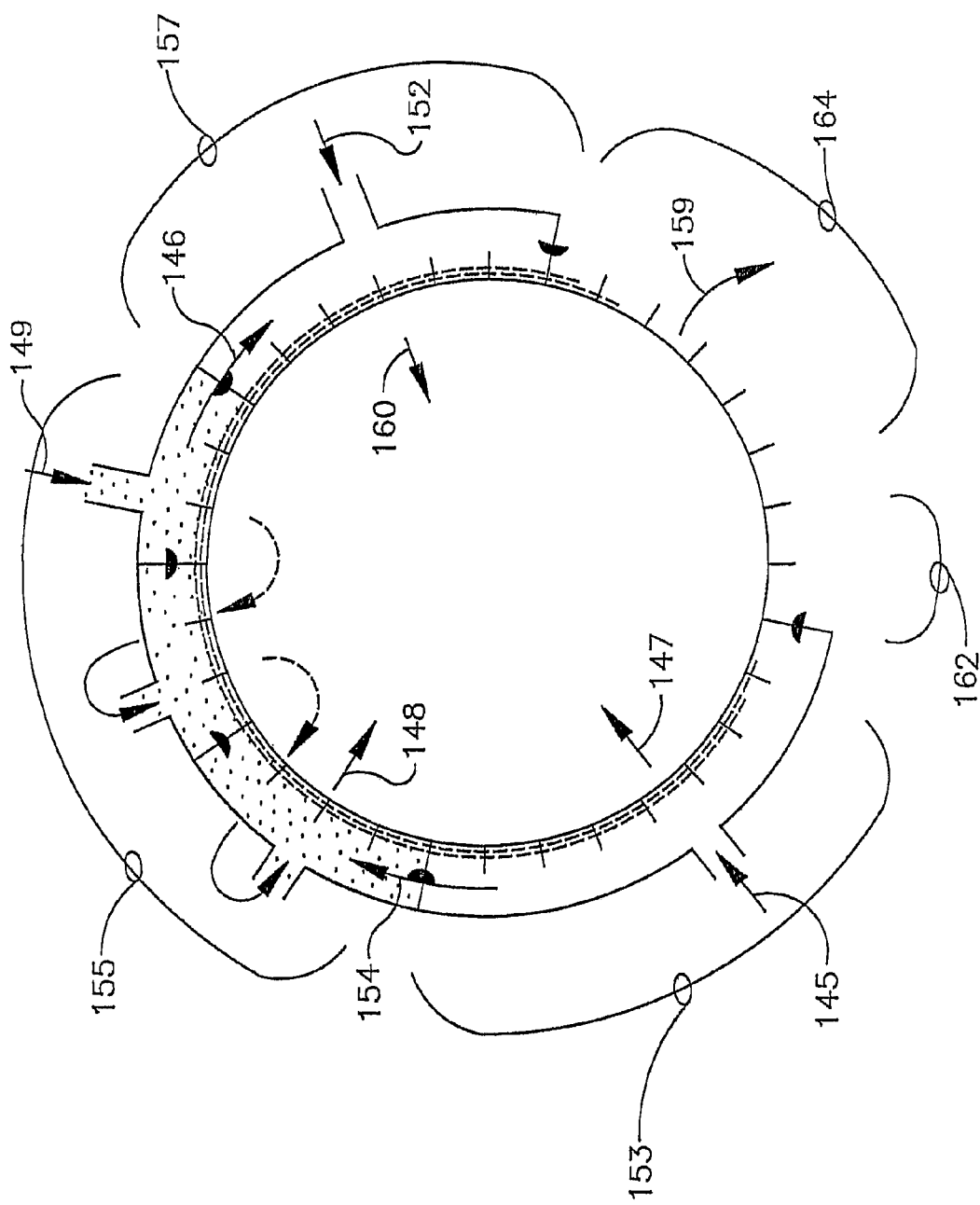
FIG. 3 illustrates an embodiment of the invention where a rotary pressure drum filter is utilized in the solid-liquid separation zone.

FIG. 3 illustrates an embodiment of the invention where a rotary pressure drum filter is utilized as the process filtration device. In an embodiment of the invention, the rotary drum pressure filter comprises a filtration zone 153, a wash zone 155, optionally, a dewatering zone 157, a discharge zone 164 and a cloth wash zone 162. The cloth wash zone shown in FIG. 3 is an embodiment of the invention where the rotary pressure drum filter comprises a cloth wash zone 162 where the filters are washed after discharge of the dewatered cake 159.

The wash filtrate 148 is produced by displacement washing the filter cake with the wash feed 149. The filter cake 154 within the solid-liquid separation zone 151 undergoes extraction of metal catalyst by introduction of the wash feed 149 to form the wash filtrate 148 wherein in an embodiment of the invention at least 80% of the metal catalyst is recovered in the wash filtrate and the mother liquor 147. In an embodiment of the invention, at least 90% of the metal catalyst is recovered in the wash filtrate 148 and the mother liquor 147. The mother liquor 147 and the wash filtrate 148 can optionally be combined before exiting the solid-liquid separation zone 151.

The wash feed 149 comprises water and optionally an additional oxidation solvent.

Perhaps most surprisingly, is that by utilizing water as a wash feed 149 at temperatures in the range of about 20° C. to about 70° C., preferably about 30° C. to about 50° C., sufficient corrosion metal is retained in the dewatered cake 159 wherein the need for corrosion metal removal by other means is eliminated. The dewatered cake 159 which represents solids stripped of metal catalyst can be disposed from the system.

Step (e) comprises mixing in a mixing zone 122 water 106 and optionally an extraction solvent 108 with a mother liquor 147 and a wash filtrate 148 to form an aqueous mixture 107. In one embodiment of the invention, the mixing zone 122 comprises a conventional mixer. If necessary, the water 106 can be added to the mixing zone 122 in sufficient quantity to dissolve the metal catalyst in the aqueous mixture stream 107.

Generally, about 0.1-1.0 parts water per part of the mother liquor 147 and wash filtrate 148 combined are sufficient to dissolve the catalyst, preferably about 0.5 to 1 parts by weight. It is desirable to keep the aqueous mixture 107 circulating with an external circulation loop. A small amount of extraction solvent 108, generally about 1 to about 10% by weight, preferably less than 5% by weight may be added to the mixing zone 122 to enhance slurry handling by reducing adherence of solids to the side of vessels. This is represented by the dashed arrow from stream 108 in FIG. 1. It is desirable, but not necessary, to subject the aqueous mixture 107, prior to extraction, to a heat treatment at about 60° C. to about 95° C., another range is about 80° C. about 90° C. for about 0.5 to about 4 hours, preferably about 1 to about 2 hours. By this treatment, organic bromides are reacted to yield inorganic bromides which are preferentially retained in the raffinate stream 110. The quantity of bromine-containing compounds purged from the system along with the unwanted impurities is thereby minimized. The heat treatment conserves bromides and simplifies disposal of the organic impurities.

Step (f) comprises contacting an extraction solvent 108 with the aqueous mixture 107 in an extraction zone 123 to form an extract stream 109 and the raffinate stream 110.

The aqueous mixture 107 is fed to an extraction zone 123 wherein the aqueous mixture 107 and the extraction solvent 108 are contacted in the extraction zone 123. The aqueous mixture 107 and the extraction solvent 108 are mixed to form an extract stream 109 comprising solvent, water, organic impurities, and extraction solvent which forms a lighter phase, and the raffinate stream 110 comprising a metal catalyst, corrosion metals, and water. The extract stream 109 is withdrawn as an overhead stream and the raffinate stream 110 is withdrawn from the bottom of extractor in extraction zone 123. In this invention, one embodiment of the extraction zone 123 is a single stage extractor.

The extraction solvent 108 used in the extractor should be substantially water-inmiscible to minimize the amount of organic solvent dissolved in the aqueous fraction. Additionally, the extraction solvent 108 is preferably an azeotropic agent which serves to assist solvent recovery from the organic extract. Solvents which have proven to be particularly useful are C1 to C6 alkyl acetates, particularly n-propyl acetate, isopropyl acetate, isobutyl acetate, sec-butyl acetate, ethyl acetate and n-butyl acetate, although other substantially water-inmiscible organic solvents having an appropriate density and a sufficiently low boiling point may also be used, such as p-xylene. N-propyl acetate and isopropyl acetate are particularly preferred due to their relatively low water miscibility and excellent azeotropic behavior.

The extraction can be effected using solvent ratios from about 1-4 parts by weight extraction solvent per part aqueous mixture. Although the extraction can be operated at ambient temperature and pressure, heating the solvent and extractor to about 30° C. to about 70° C., another range of about 40° C. to about 60° C. can be used. Although the extract stream 109 comprises small amounts of the metal catalyst and corrosion metals, essentially all of the metal catalyst and the majority of the remaining corrosion metals are contained in the heavier phase, raffinate stream 110.

Step (g) comprises separating the extract stream 109 in a separation zone 124 to form a high boiling point organic impurities stream 115 and a recovered extraction solvent stream 117.

The extract stream 109 comprises organic solvent and organic impurities. The extract stream 109 can further comprises acetic acid and water, often in minor amounts. The extract stream 109 may be distilled in a separation zone 124 comprising conventional distillation equipment. Convention distillation equipment includes, for example, a distillation column.

Most of the organic impurities are extracted by the organic solvent in the extraction zone, 123. This occurs because the organic impurities show a high degree of solubility for the organic solvent and to a lesser extent for acetic acid. By distilling the lighter phase from the extractor, the organic solvent is evaporated allowing the organic impurities to concentrate in the column underflow.

The recovered extraction solvent stream 117 may be recycled to the extractor in the extraction zone 123. The high-boiling organic impurities stream 115 are removed as sludge from the base of the distillation column for disposal.

EXAMPLES

This invention can be further illustrated by the following examples of other embodiments thereof, although it will be understood that these examples are included merely for purposes of illustration and are not intended to limit the scope of the invention unless otherwise specifically indicated.

Example 1

The objective of these examples is to illustrate the recovery of cobalt catalyst from a super concentrated purge slurry 145 with minimum of wash feed 149. The following example illustrates the capability of vacuum filtration using a lab scale Buchner type filter. Data generated below is applicable to batch or continuous vacuum filters.

The lab scale filtration apparatus consists of a Buchner filter with 100 cm² of filter area placed on top of a 4 liter vacuum flask. The vacuum system provides 0.6 bar of vacuum at a flux rate of approximately 150 m³/h per m² filtration area. The vacuum system is turned on and 600 grams of 40° C. slurry containing 20% solids of super concentrated purge slurry 145 is charged to the filter. The time for filter cake 154 to first appear is recorded (dry top time). The filter cake 154 is allowed to dewater for another 10 seconds. A specific amount of 40° C. wash feed 149 comprising water is then poured on top of the filter cake 154. The time for filter cake 154 to appear after addition of the wash feed 149 is recorded. The filter cake 154 is allowed to dewater for additional 20 seconds. The filter cake 154 height, filter cake 154 mass, filter cake 154 percentage moisture, mother liquor 147 mass, and mass of wash filtrate 148 mass is recorded. Dewatered cake samples are subjected to cobalt weight percentage analysis.

The procedure outline above was repeated 6 times with the wash ratio ranging from 0 to 5. Wash ratio is defined as the grams of water feed 149 per gram of dry solid in the filter cake 154. The wt % of cobalt in the washed cake with corresponding wash ratios is shown in Table 1 below:

TABLE 1

| Wash Ratio | Cobalt Wt % |
|---|---|
| 0 | 2.93% |
| 1 | 2.37% |
| 2 | 0.78% |
| 3 | 0.36% |
| 4 | 0.05% |
| 5 | 0.03% |

Severe filter cake 154 cracking was observed just after reaching dry top in each experiment, resulting in no visible filter cake 154 dewatering after reaching dry top. The resulting cakes had an average moisture of 56%.

Example 2

The following example illustrates the capability of pressure filtration using a 1 liter lab scale BHS-FEST™ pressure filter.

The lab scale apparatus consists of a 1 liter lab scale BHS-FEST™ pressure filter with 20 cm² of filter area. A 1 liter beaker on a balance is positioned below the pressure filter to receive the mother liquor and wash filtrate. Pressurized nitrogen supplied 2 bar flows into the filter after adding the super concentrated purge slurry 145.

89 grams of a 20% solids super concentrated purge slurry 145 is charged to the filter. Mother liquor is collected in the 1 liter beaker. After 7 seconds, nitrogen breakthrough occurs. The nitrogen flow is stopped, the filter is opened, and 39 grams of 40° C. wash feed 149 is added. The filter is sealed and the nitrogen flow is started. After 30 seconds, gas breakthrough occurs, and another 30 seconds of nitrogen flow is allowed for washed cake 146 dewatering. The dewatered cake 159 is removed from the filter and the resulting % cake moisture is 40% moisture. The results of the pressure filtration are shown below.

TABLE 2

| Wash Ratio | Cake Cobalt Wt. % |
|---|---|
| 2 | 0.13 |

In contrast, vacuum filtration from example 1 requires a wash ratio of 3.75 to achieve a cake cobalt level of 0.13 wt. % where as pressure filtration from example 2 only requires a wash ratio of about 2. Vacuum filtration requires 87% more wash water that pressure filtration.

We claim:

1. A process comprising:
   (a) filtering a super concentrated oxidizer purge slurry comprising a metal catalyst in a solid-liquid separation zone to form a filter cake and a mother liquor wherein said super concentrated oxidizer purge slurry is produced by the concentration of an oxidizer purge stream;
   (b) washing said filter cake with a wash feed in said solid-liquid separation zone to form a washed cake and a wash filtrate; and optionally dewatering said wash filtrate in said solid-liquid separation zone to form a dewatered cake; wherein said solid-liquid separation zone comprises at least one pressure filtration device; wherein at least 80% of said metal catalyst from said super concentrated oxidizer purge slurry is recovered through said separation zone into said mother liquor and said wash filtrate cumulative.

2. The process according to claim 1 wherein said pressure filtration device operates at a temperature between about 25° C. to about 160° C.

3. The process according to claim 2 wherein said pressure filtration device is operated at a pressure of about 1 atmosphere to about 50 atmospheres.

4. The process according to claim 1 wherein said pressure filtration device comprises at least one filter cell and wherein at least one filter cell accumulates at least 0.25 inch in depth of said filter cake.

5. The process according to claim 1 wherein said pressure filtration device comprises at least one filter cell and wherein at least one filter cell accumulates at least 0.5 inch in depth of said filter cake.

6. The process according to claim 1 wherein said pressure filtration device comprises at least one filter cell and wherein at least one filter cell accumulates at least 1 inch in depth of said filter cake.

7. The process according to claim 4, 5, or 6 wherein there is a reservoir over said filter cake which is at least 0.25 inch in depth.

8. The process according to claim 4, 5 or 6 wherein said pressure filtration device operates at a temperature between about 25° C. to about 160° C.

9. The process according to claim 8 wherein said pressure filtration device is operated at a pressure of about 1 atmosphere to about 50 atmospheres.

10. The process according to claim 8 wherein said dewatering results in said dewatered cake having a moisture content from about 10% to about 50%.

11. The process according to claim 1, 2, 3 or 4 wherein said pressure filtration device is a rotary pressure drum filter.

* * * * *